(12) United States Patent
Kelley

(10) Patent No.: US 10,172,622 B2
(45) Date of Patent: Jan. 8, 2019

(54) APPLICATOR INSTRUMENT WITH FOLDING STAPLING TIP

(71) Applicant: Jill Kelley, Tampa, FL (US)

(72) Inventor: Jill Kelley, Tampa, FL (US)

(*) Notice: Subject to any disclaimer, the term of this patent is extended or adjusted under 35 U.S.C. 154(b) by 363 days.

(21) Appl. No.: 15/143,014

(22) Filed: Apr. 29, 2016

(65) Prior Publication Data

US 2016/0317146 A1  Nov. 3, 2016

Related U.S. Application Data

(60) Provisional application No. 62/155,493, filed on May 1, 2015.

(51) Int. Cl.
*A61B 17/068* (2006.01)
*A61B 17/10* (2006.01)
*A61B 17/115* (2006.01)

(52) U.S. Cl.
CPC ................................. *A61B 17/1155* (2013.01)

(58) Field of Classification Search
None
See application file for complete search history.

(56) References Cited

U.S. PATENT DOCUMENTS

| 4,505,414 A * | 3/1985 | Filipi ................... | A61B 17/115 227/155 |
| 5,839,639 A * | 11/1998 | Sauer ................... | A61B 17/115 227/175.1 |
| 8,328,063 B2 * | 12/2012 | Milliman ............ | A61B 17/1114 227/175.1 |
| 2004/0195289 A1 * | 10/2004 | Aranyi ................. | A61B 17/072 227/180.1 |
| 2006/0201989 A1 * | 9/2006 | Ojeda .................... | A61B 17/11 227/175.1 |
| 2012/0234891 A1 * | 9/2012 | Aronhalt ............ | A61B 17/1155 227/175.1 |

* cited by examiner

*Primary Examiner* — Nathaniel C Chukwurah
*Assistant Examiner* — Tanzim Imam
(74) *Attorney, Agent, or Firm* — Vincent G. LoTempio; Kloss, Stenger & LoTempio; David T. Stephenson

(57) ABSTRACT

An applicator instrument has a body portion that has at least one trigger mechanism and a rod extending from the body portion. The applicator instrument has a folding cap mechanism installed or inserted into an end of the rod. The folding cap mechanism has a plurality of extension arms, each of which have a staple clinch bucket. The extension arms are coupled to a trigger of the triggers and are movable between a collapsed position and an extended position by the trigger.

10 Claims, 6 Drawing Sheets

APPLICATOR INSTRUMENT WITH FOLDING STAPLING TIP

CROSS REFERENCE TO RELATED APPLICATION

This application claims the benefit of U.S. Provisional Application No. 62/155,493, filed May 1, 2015, having the title for APPLICATOR INSTRUMENT WITH FOLDING STAPLING TIP.

FIELD OF THE INVENTION

This invention relates to the field of medicine and more particularly to an applicator instrument with staple system and further, to an applicator instrument for anastomosis between two tubes having an extension that folds like an umbrella.

BACKGROUND

Various types of surgical staplers are known for repair of tears or separations in tissue. The use of various types of staplers has been used in gastric, colon, rectal, and/or esophageal surgery, for example, in gastric reconstructions performed end-to-end, end-to-side, or side-to-side.

The hand-sewn anastomosis has largely been replaced by the EEA (end to end anastomosis) stapling especially in colorectal and gastric bypass operations. For example, stapling the proximal colon to the lower rectum is easier to perform, and results in a similar anastomotic leak rate when compared to hand-sewn anastomosis.

The circular stapling device consists of an actuating head portion attached to an elongated tubular body with a handle on the opposed end of the body from the head. The anvil functions essentially as an end plate to turn in and close the ends of the staples. In one example of such a device, an instrument such as that disclosed in U.S. Pat. No. 5,119,983 is used to create an anastomosis. In this device, an anvil assembly is positioned on the end of a rod which is retracted within a tubular housing of the instrument. This instrument is introduced into the lumen of a stomach without the anvil in place, and then the tip of the center rod is passed through an opening which has been made at the anastomotic site and the anvil is then be secured on the end of the center rod. Alternately, the anvil is inserted into the intestine for securement to the rod and the end of the duodenum is then sutured off about the rod. Next, the rod is retracted towards the instrument to clamp the tissue between the anvil and the stapler body and then staples from the instrument are forced through the tissue and against the anvil so as to join the two sections of intestine to be joined such as the colon to the rectum or the stomach to the intestine positioned there between. With such a system, a relatively large incision need be made with attendant trauma to tissue and associated complications. The larger the hole, the less tissue available for staples to set. If the hole is too large, then some of the staples within the circular anastomosis are at risk to misfire and not land within tissue at all, thus causing leakage.

Even though current methods use detachable anvils; the insertion of the detachable anvil into the patient's body is still typically performed through a relatively large incision during open surgery and laparoscopic surgery. The smaller the opening in the recipient tissue made for anvil insertion, the more tissue available for the rows of staples in the circular anastomosis.

The tissue stapled together leaves a smaller opening than the original lumen into which the anvil and stapler were inserted. In order to insert the anvil through the smallest possible defect, it is desirable to provide an anvil which can be collapsed to introduce the anvil into the body through a relatively small incision and for removal of the anvil after stapling through the smaller opening between the staples.

What is needed is an applicator instrument with either a stationary or removable anvil that collapses to a small enough diameter enabling insertion and removal through small orifices to maximize tissue available for the staples to approximate the tissue.

SUMMARY

In order to eliminate the disadvantages of the state of the art, an object of the present invention is an applicator instrument with either a stationary or removable folding cap mechanism that collapses to a small enough diameter enabling insertion and removal through small orifices to maximize tissue available for the staples to approximate the tissue in an anastomosis procedure.

A further object of the present invention is that it has folding cap mechanism that can be made to go through a smaller space by reducing the surrounding area when it's arms are extended or retracted.

A further object of the present invention is that the folding cap mechanism can be produced in a detachable manner on the main body of the instrument.

A further object of the present invention is that it provides advantage in both open and laparoscopic interventions.

A further object of the present invention is to provide a folding cap mechanism that folds up like an umbrella that makes a very tiny hole when inserted rather than the big circular anvil that one must then either create a purse-string suture to approximate the tissue around it (or insert it first, staple across the bowel and poke it through the intestine afterward).

The present invention generally comprises an applicator instrument that has a folding cap mechanism installed or inserted into an end of a rod. The folding cap mechanism has a plurality of extension arms, each of which have a staple clinch bucket. The extension arms are coupled to a trigger of the triggers and are movable between a collapsed position and an extended position by the trigger.

These and other objects, features and advantages of the present invention will become readily apparent to those having ordinary skill in the art upon a reading of the following detailed description in view of the appended claims and drawings

BRIEF DESCRIPTION OF DRAWINGS

The invention can be best understood by those having ordinary skill in the art by reference to the following detailed description when considered in conjunction with the accompanying drawings in which.

DETAILED DESCRIPTION OF THE EMBODIMENTS

Figure 1:
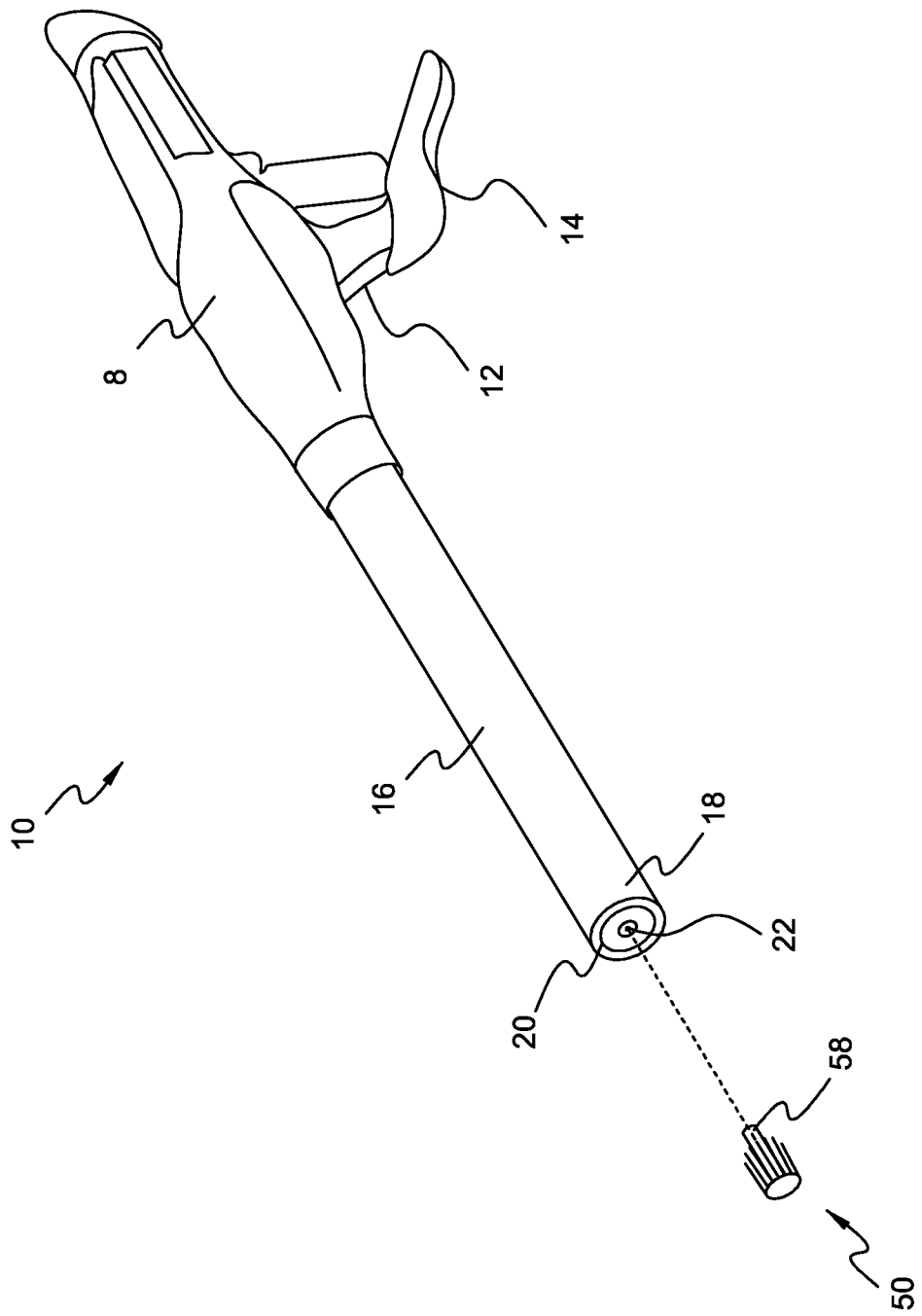
FIG. 1 illustrates a perspective view of an applicator instrument with folding stapling tip.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

It should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

Throughout this description, the stapling function of the applicator instrument is described, though it is fully anticipated that the applicator instrument performs other functions including, but not limited to, cutting tissue, clamping tissue, cauterizing, etc.

Referring to FIG. 1, a perspective view of an applicator instrument 10 with folding cap mechanism 50 is shown. The body portion 8 of the stapler 10 is, for example, similar to other such staplers as known in the industry, for example, the applicator instrument (e.g., stapler, cutter, tissue clamp) disclosed in U.S. Pat. No. 5,839,639 which is here in incorporated by reference. In this example, the body portion 8 is shown with two trigger mechanisms 12/14. The first trigger mechanism 12 is operated to extend/retract the folding cap mechanism 50 and the second trigger mechanism 14 is operated to effect an operation such as stapling, cutting, cauterizing, etc. It is fully anticipated that more or less features such as the trigger mechanisms 12/14 are provided for actuation of different features, or different degrees of operation of the trigger mechanisms 12/14 effect such operations. For example, moving the second trigger mechanism 14 half-way initiates clamping while moving the second trigger mechanism 14 further initiates stapling, etc. Additionally, various locks and interlocks are also anticipated and not shown for clarity purposes.

Figure 4:
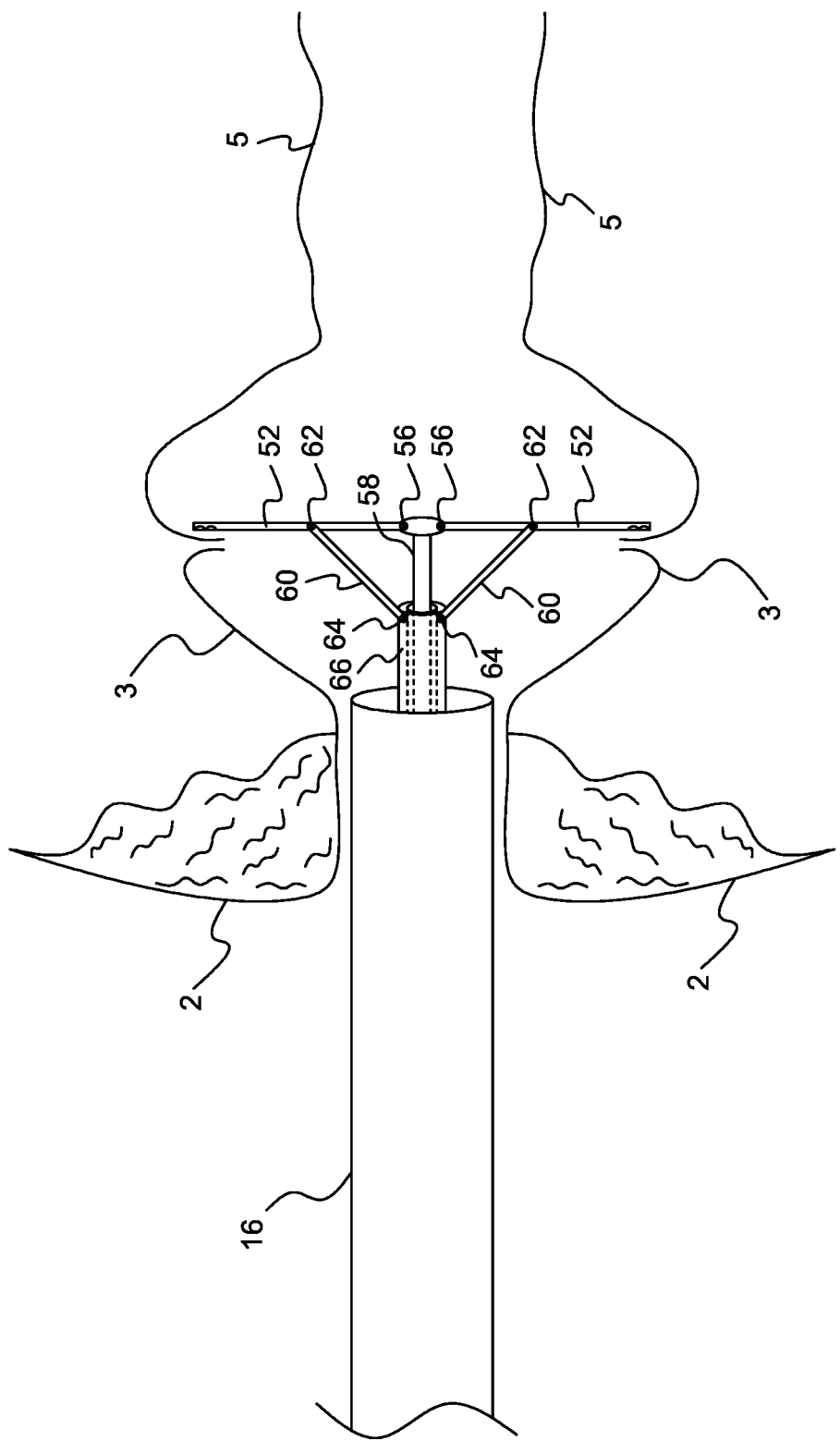
FIG. 4 illustrates a plan view of the rod of the applicator instrument within a body orifice, the folding stapling tip in a configuration ready for stapling tissue.
Figure 5:
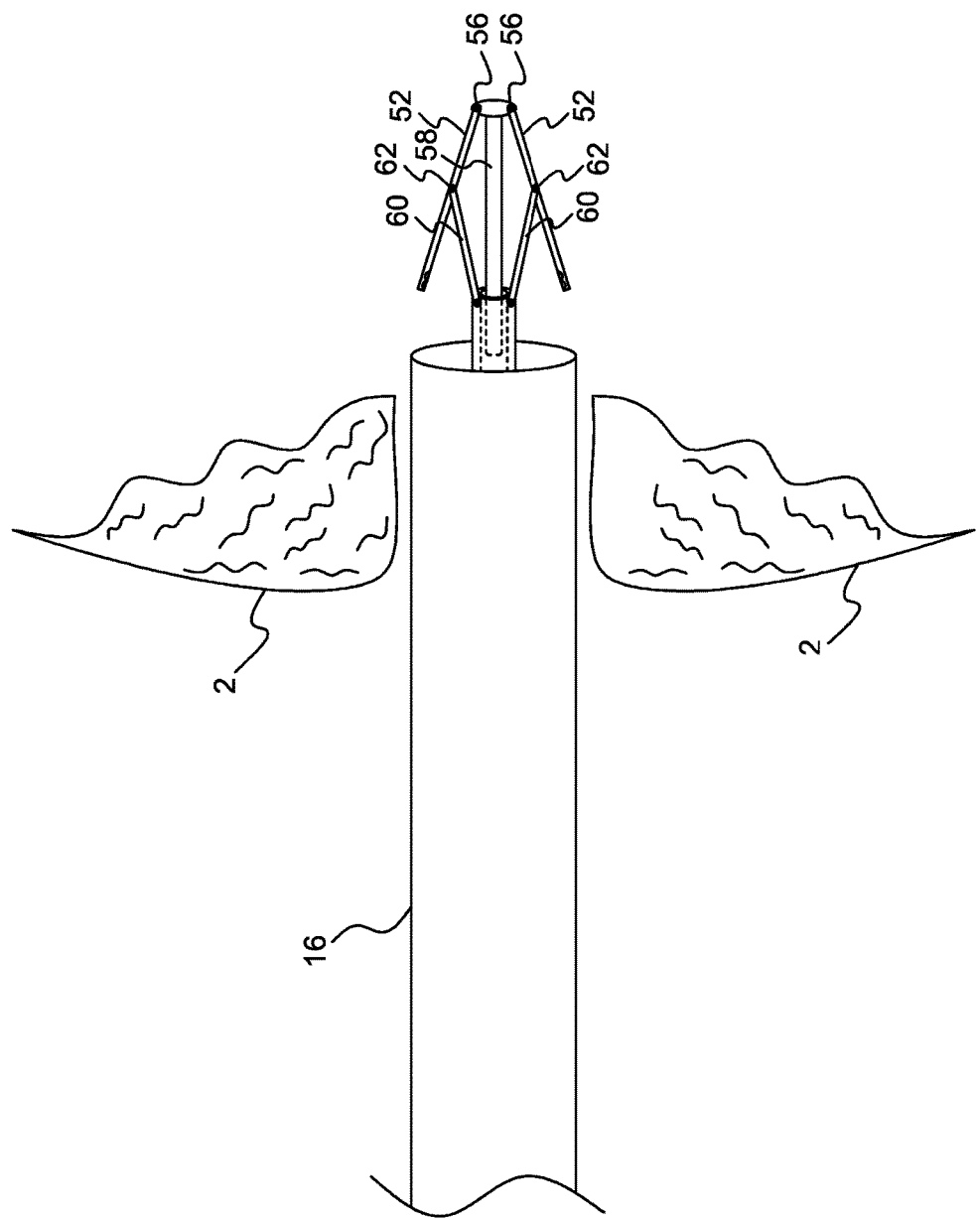
FIG. 5 illustrates a plan view of the rod of the applicator instrument within a body orifice, the folding stapling tip in a configuration ready for extraction from the body orifice.
Figure 6:
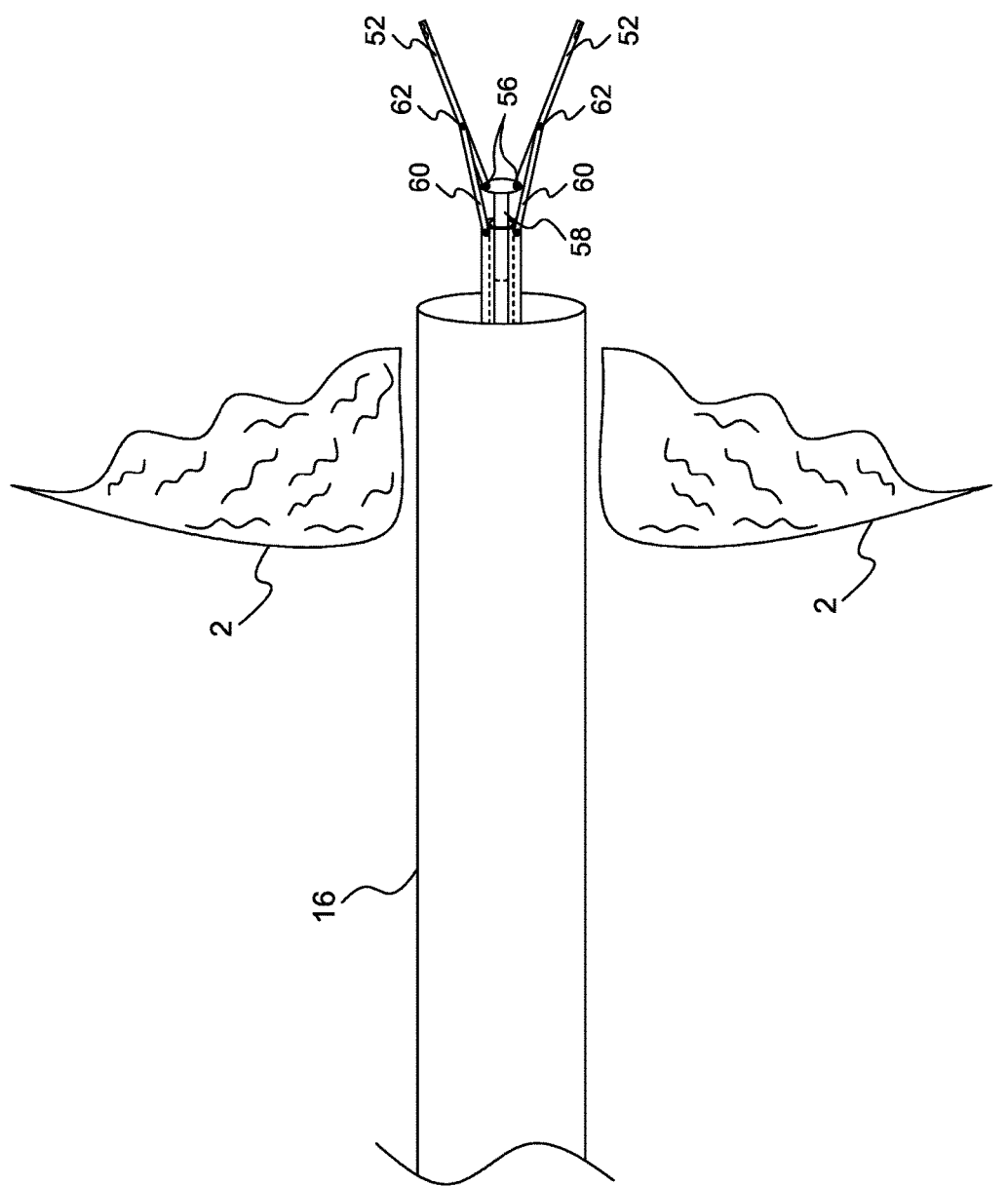
FIG. 6 illustrates a plan view of the rod of the applicator instrument within a body orifice, the folding stapling tip in a second configuration ready for extraction from the body orifice.

The rod 16 of the applicator instrument 10 is typically elongated and tubular so that the rod 16 is insertable and fits within a specific orifice of a body, such as the anus and bowel 2 of a human body (see FIGS. 4-6). In some embodiments, the folding cap mechanism 50 is removable from the rod 16, as shown in FIG. 1, while in other embodiments, the folding cap mechanism 50 is fixed to the rod 16 and is not removed during operation (not shown).

At the insertion end 18 of the rod 16, one exemplary interface for the folding stapling tip 50 is shown, including a receiver 22 into which the main shaft 58 of the folding stapling tip 50 is inserted and an actuator 20 arm that interfaces with the extension mechanism 66 of the folding cap mechanism 50 (see FIGS. 2-6). It is anticipated that a trigger 12/14 of the applicator instrument 10 initiates linear movement of the actuator arm 20 to extend/retract the folding cap mechanism 50.

Figure 2:
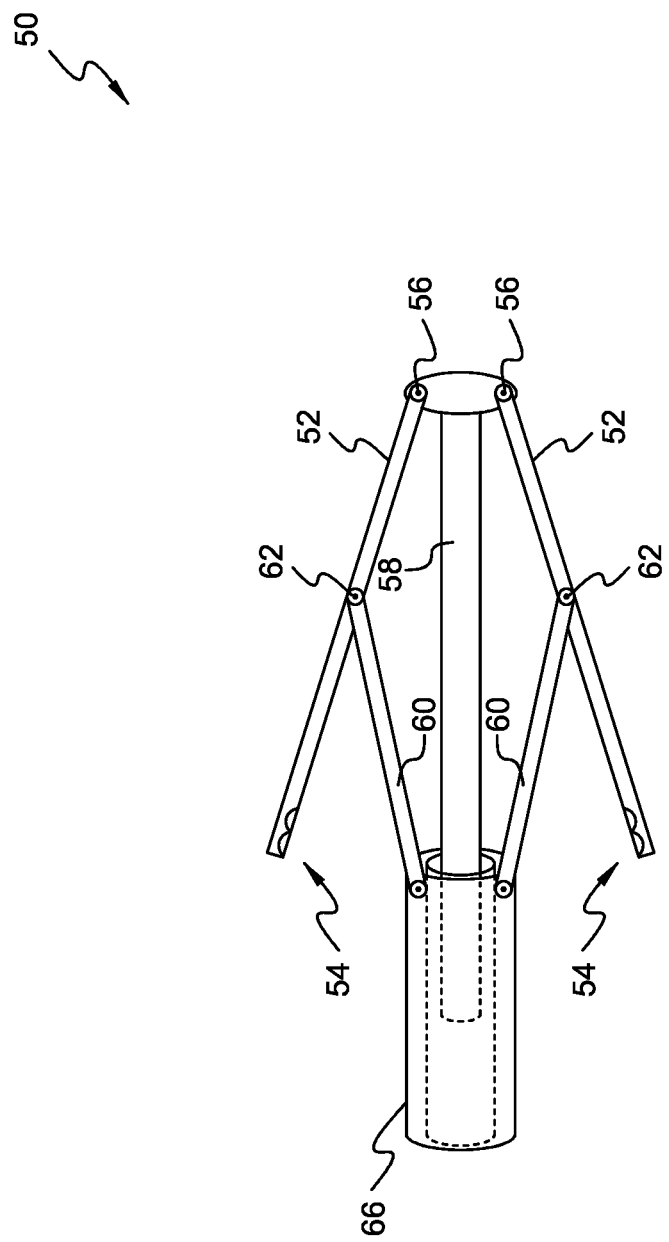
FIG. 2 illustrates a plan view of the folding stapling tip in a retracted configuration.
Figure 3:
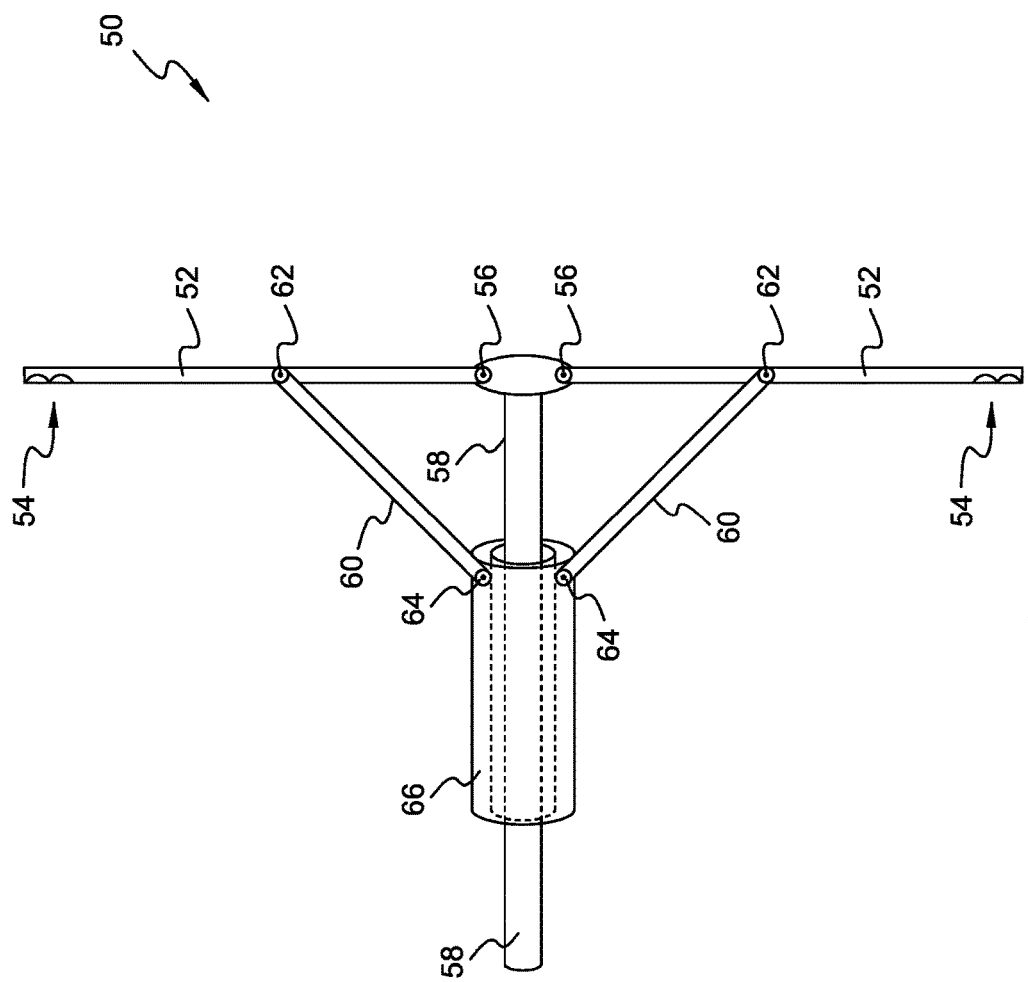
FIG. 3 illustrates a plan view of the folding stapling tip in a configuration ready for stapling tissue.

Referring to FIGS. 2 and 3, plan views of the folding cap mechanism 50 are shown in a retracted configuration (FIG. 2) and in a configuration ready for stapling tissue (FIG. 3). The folding cap mechanism 50 includes any number of extension arms 52, similar to ribs of an umbrella. Any or all extension arm 52 include one or more staple clinching buckets 54. The staple clinching buckets 54 function similar to staple clinching buckets on a paper stapler, bending the extending portion of the staples to hold two or more items together (papers for paper staples, tissue for the applicator instrument 10). The extension arms 52 rotatably interface to the main shaft 58 by pivots 56, enabling the extension arms 52 to open/close as would ribs of an umbrella.

In FIG. 2, the extension mechanism 66 is in a retracted position, pulled in a direction of the body portion 8. In this mode, the extension arms 52 are pulled into the retracted position (as shown in FIG. 2) by angled arms 60 that are connected between the extension arms 52 and the extension mechanism 66 with pivots 62/64.

In FIG. 3, the extension mechanism 66 is in an extended position, moved in a direction away from the body portion 8 a specific distance such that the extension arms 52 are pushed into the extended position (as shown in FIG. 3) to be approximately at right angles with respect to the main shaft 58 by angled arms 60 that are connected between the extension arms 52 and the extension mechanism 66 with the pivots 62/64.

Referring to FIGS. 4, 5, and 6, plan views of the rod of the applicator instrument 10 within a body orifice 2 are shown. In FIG. 4, the folding cap mechanism 50 is in a configuration ready for stapling tissue. In FIG. 5, the folding cap mechanism 50 is in a configuration ready for extraction from the body orifice, and In FIG. 6, the folding cap mechanism 50 is in a second configuration ready for extraction from the body orifice.

Although there is no limitation of the use of the applicator instrument 10, the rod 16 of the applicator instrument 10 is shown inserted into an anal opening 2 of a body, for example, a human body. In FIG. 4, the folding cap mechanism 50 is extended and, as an example, the bowel 3 is shown being stapled (anastomosis) to the large intestine 5. After the staple operation is finished, one can see that the resulting opening through which the folding cap mechanism 50 must travel is considerable smaller than the extended extension arms 52 and extraction of the rod 16 of the applicator instrument 10 in this configuration is not possible without the possibility of causing trauma to the anastomosis that potentially results in leakage. After anastomosis, the folding cap mechanism 50 cannot be detached from the rod 16 of the applicator instrument because there is no opening through which the folding cap mechanism 50 can be removed.

Therefore, the folding cap mechanism 50 is made smaller by retracting the extension arms 52 (like a folded umbrella) as shown in FIG. 5 or further extending the extension arms 52 (like an umbrella caught in too much wind) as shown in FIG. 6. In the configurations of FIGS. 5 and 6, it is possible to remove the rod 16 of the applicator instrument 10 with the folded cap mechanism 50, whereas the folding cap mechanism 50 smoothly transitions through the anastomosis and through the anus 2.

In one mode of operation, the rod 16 of the applicator instrument 10 is inserted through the anus and the folding cap mechanism 50 is inserted into the body through a secondary opening and attached to the rod 16 of the applicator instrument 10. In another mode of operation, the folding cap mechanism 50 is already attached to the rod 16 of the applicator instrument 10 while the rod 16 of the applicator instrument 10 with the folding cap mechanism 50 attached there to is inserted through the anus 2.

The extension arms 52 are extended (e.g., to be at approximately right angles to the main shaft 58). Tissue, for example, of the bowel 3 is overlapped with tissue of the large intestine 5 and staples are pushed out of the rod 16, through the tissue 3/5 and the ends of the staples are bent by the staple clinching buckets 54, forming the anastomosis. As the opening in the anastomosis is too small for passing of the extended extension arms 52, the extension arms 52 are pulled back (as in FIG. 5) or pushed further out (as in FIG. 6) and the rod 16 of the applicator instrument 10 with the folding cap mechanism 50 in a compressed mode is extracted from the anus 2.

Any number extension arms 52 and staple clinch buckets 54 are anticipated to provide one row, two rows, in-line, staggered staples as needed for any specific anastomosis. Although, not shown, other capabilities are anticipated such as cutting of the tissue (either before anastomosis or after anastomosis), cauterization, clamping/holding of tissue 3/5, etc.

Equivalent elements can be substituted for the ones set forth above such that they perform in substantially the same manner in substantially the same way for achieving substantially the same result.

The extension arms 52 are extended (e.g., to be at approximately right angles to the main shaft 58). Tissue, for example, of the bowel 3 is overlapped with tissue of the large intestine 5 and staples are pushed out of the rod 16, through the tissue 3/5 and the ends of the staples are bent by the staple clinching buckets 54, forming the anastomosis. As the opening in the anastomosis is too small for passing of the extended extension arms 52, the extension arms 52 are pulled back (as in FIG. 5) or pushed further out (as in FIG. 6) and the rod 16 of the applicator instrument 10 with the folding cap mechanism 50 in a compressed mode is extracted from the anus 2.

Any number extension arms 52 and staple clinch buckets 54 are anticipated to provide one row, two rows, in-line, staggered staples as needed for any specific anastomosis. Although, not shown, other capabilities are anticipated such as cutting of the tissue (either before anastomosis or after anastomosis), cauterization, clamping/holding of tissue 3/5, etc.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An applicator instrument comprising: a body portion having at least one trigger mechanism and having a rod extending from the body portion; and a folding cap mechanism at an end of the rod, the folding cap mechanism having a main shaft and a plurality of extension arms, each extension arm having a staple clinch bucket, the extension arms coupled to the at least one trigger mechanism, the extension arms movable between a collapsed position and an extended position by the at least one trigger mechanism; wherein the extension arms each have a first end and a second end; wherein the first end of each of the extension arms is connected to one of a plurality of first end pivots; wherein the first end pivots are located at a terminus of the main shaft; wherein the second end of each of the extension arms is free; wherein the extension arms each have a pivot attached to one of a plurality of angled arms between the first and second ends of the extension arms; and wherein the extension arms are adapted for pivotally rotating from the collapsed position forming an angle of less than 90 degrees between the extension arms and the main shaft, to the extended position, forming an angle of 90 degrees between the extension arms and the main shaft, to a hyperextended position forming an angle of greater than 90 degrees between the extension arms and the main shaft.

2. The applicator instrument of claim 1, wherein the folding cap mechanism is affixed to an end of the rod.

3. The applicator instrument of claim 1, wherein the folding cap mechanism is affixed to an end of the rod after the rod is inserted into a body through an orifice of the body.

4. The applicator instrument of claim 3, wherein the folding cap mechanism is removable.

5. The applicator instrument of claim 4, wherein said rod has: a stapler holding assembly to store a plurality of staples at a distal end of said rod; and a frame member having means for mounting said folding cap mechanism.

6. The applicator instrument of claim 1, wherein the plurality of extension arms comprises two extension arms to provide two in-line rows of staggered staples as needed for an anastomosis.

7. The applicator instrument of claim 1, wherein the extension arms are pushed into the extended position at right angles with respect to an extension mechanism of the folding cap mechanism by said angled arms that are connected with pivots to the extension arms and to the extension mechanism.

8. The applicator instrument of claim 1, wherein the extension arms rotatably interface with the main shaft by the first end pivots.

9. The applicator instrument of claim 1, wherein the extension arms are operatively arranged to cut tissue.

10. The applicator instrument of claim 1, wherein the extension arms are operatively arranged to rotate.

* * * * *